(12) United States Patent
Chien (10) Patent No.: US 9,782,102 B2
(45) Date of Patent: Oct. 10, 2017

(54) ELECTROCARDIOGRAPHY TO DIFFERENTIATE ACUTE MYOCARDIAL INFARCTION FROM BUNDLE BRANCH BLOCK OR LEFT VENTRICULAR HYPERTROPHY

(71) Applicant: KONINKLIJKE PHILIPS N.V., Eindhoven (NL)

(72) Inventor: Cheng-Hao Chien, Thousand Oaks, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 10 days.

(21) Appl. No.: 14/666,861

(22) Filed: Mar. 24, 2015

(65) Prior Publication Data

US 2016/0143553 A1    May 26, 2016

Related U.S. Application Data

(60) Provisional application No. 62/082,836, filed on Nov. 21, 2014.

(51) Int. Cl.
*A61B 5/04*     (2006.01)
*A61B 5/0472*   (2006.01)
(Continued)

(52) U.S. Cl.
CPC ........ *A61B 5/0472* (2013.01); *A61B 5/04011* (2013.01); *A61B 5/04012* (2013.01);
(Continued)

(58) Field of Classification Search
None
See application file for complete search history.

(56) References Cited

U.S. PATENT DOCUMENTS

| 7,072,708 | B1 | 7/2006 | Andresen et al. |
| 2008/0114257 | A1* | 5/2008 | Molin ............... A61B 5/04011 600/512 |

(Continued)

OTHER PUBLICATIONS

Brady et al: "ECG Patterns Confounding the ECG Diagnosis of Acute Coronary Syndrome: Left Bundle Branch Block, Right Ventricular Paced Rythms, and Left Ventricular Hypertrophy"; Emerg Med Clin N Am, 23 (2005) 999-1025.

(Continued)

*Primary Examiner* — Brian T Gedeon
*Assistant Examiner* — Ankit D Tejani (57) ABSTRACT

Acute myocardial infarction (AMI) is diagnosed if: (1) the ECG traces satisfy an ST Elevation Myocardial Infarction (STEMI) criterion and the ECG traces do not indicate the subject has a confounding cardiac condition, or (2) the ECG traces satisfy the STEMI criterion and the ECG traces also indicate the subject has the confounding cardiac condition and a three-dimensional vector cardiograph (3D-VCG) signal generated from the ECG traces includes an ST vector in the ST segment of the 3D-VCG signal and a terminal QRS vector of maximum magnitude in a terminal portion of the QRS complex of the 3D-VCG signal for which the angle between the ST vector and the terminal QRS vector is less than a threshold angle, e.g. in the range [130°, 170°] inclusive. The confounding cardiac condition may be bundle branch block (BBB), left ventricular hypertrophy (LVH), or interventricular conduction delay (IVCD).

23 Claims, 6 Drawing Sheets

(51) Int. Cl.
*A61B 5/00* (2006.01)
*A61B 5/0432* (2006.01)
*A61B 5/0408* (2006.01)

(52) U.S. Cl.
CPC ............ *A61B 5/746* (2013.01); *A61B 5/0408* (2013.01); *A61B 5/0432* (2013.01)

(56) References Cited

U.S. PATENT DOCUMENTS

| | | | |
|---|---|---|---|
| 2010/0298729 A1* | 11/2010 | Zhang | A61B 5/0452 600/512 |
| 2011/0112415 A1 | 5/2011 | Bojovic et al. | |
| 2012/0041328 A1* | 2/2012 | Rajagopalan | A61B 5/0452 600/523 |
| 2013/0096447 A1 | 4/2013 | Dhawan et al. | |
| 2014/0107501 A1* | 4/2014 | Komanduri | A61B 5/0205 600/484 |

OTHER PUBLICATIONS

Hartman et al: "The Use of a 4-Step Algorithm in the Electrocardiographic Diagnosis of ST-Segment Elevation Myocardial Infarction by Novice Interpreters"; American Journal of Emergency Medicine (2012) 30, pp. 1282-1295.

Pollak et al: "Electrocardiographic Patterns Mimicking ST Segment Elevation Myocardial Infarction"; Cardiol Clin 30 (2012), pp. 601-615.

Wang et al: "ST-Segment Elevation in Conditions Other Than Acute Myocardial Infarcton"; New England J Med, vol. 349, Issue 22, pp. 2128-2135.

Sgarbossa et al: "Electrocardiographic Diagnosis of Evolving Acute Myocardial Infarction in the Presence of Left Bundle-Branch Block"; The New England Journal of Medicine, Feb. 22, 1996, vol. 334, No. 8, pp. 481-487.

Gregg et al: "Combining Sgarbossa and Selvester ECG Criteria to Improve Stemi Detection in the Presence of LBBB"; Computing in Cardiology 2010, vol. 37, pp. 277-280.

Kontos et al: "Can Myocardial Infarction Be Rapidly Identified in Emergency Department Jatients Who Have Left Bundle-Branch Block?":Annals of Emergency Medicine, May 2001, vol. 37:5, pp. 431-438.

Pope et al: "The Impact of Electrocardiographic Left Ventricular Hypertrophy and Bundl: Branch Block on the Triage and Outcome of Ed Patients With a Suspected Acute Coronary Syndrome: a Multicenter Study"; Am J Emerg Med, 2004, vol. 22, pp. 156-163.

Tabas et al: "Electrocardiographic Criteria for Detecting Acute Myocardial Infarction in Patients With Left Bundle Branch Block: a Meta-Analysis"; Annals of Emergency Medicine, 2008, vol. 52, No. 4, pp. 329-336.

Wagner et al: "AHA/ACCF/HRS Recommendations for the Standardization and Interpretation of the Electrocardiogram"; Journal of the American College of Cardiology, 2009, vol. 53(11), pp. 1003-1011.

* cited by examiner

ELECTROCARDIOGRAPHY TO DIFFERENTIATE ACUTE MYOCARDIAL INFARCTION FROM BUNDLE BRANCH BLOCK OR LEFT VENTRICULAR HYPERTROPHY

This application claims the benefit of U.S. Provisional Application 62/082,836, filed on Nov. 21, 2014.

The following relates generally to cardiac care arts, electrocardiograph arts, and related arts.

Acute myocardial infarction (AMI) occurs when blood flow to the heart is blocked, usually due to an obstructive lesion in a coronary artery, leading to heart muscle injury because of lack of oxygen. AMI is colloquially referred to as a "heart attack". Elevation of the ST segment of the electrocardiogram (ECG) is associated with AMI, and hence is also referred to as ST Elevation Myocardial Infarction (STEMI). STEMI requires immediate, aggressive treatment to restore blood flow to the heart in order to prevent permanent injury or death. On the other hand, AMI that is not associated with ST elevation (i.e., NSTEMI) is generally considered a less acute condition requiring less aggressive treatment.

Diagnosis of AMI relies upon physical symptoms such as chest pain in combination with ECG analysis. As just noted, an elevated ST segment is the conventional diagnostic of AMI—however, AMI is not the only condition that impacts ST level. Other conditions that can lead to ST segment deviation include bundle branch block (BBB) and left ventricular hypertrophy (LVH). The BBB condition refers to a defect in electrical conduction through the heart from its natural pacemaker, the sinoatrial node. BBB can be classified based on which side of the heart is affected, the left bundle (LBBB) or right bundle (RBBB). LBBB generally causes ST elevation in the right precordial leads V1, V2 and V3, while RBBB causes ST depression in those leads. The ST level is usually not used to diagnose BBB—rather, a broadened QRS complex is usually considered to be diagnostic of BBB. The LVH condition refers to a thickening of the myocardial muscle of the left ventricle of the heart. LVH also leads to ST elevation in the right precordial leads, but again this is usually not relied upon (at least solely) to diagnose LVH. Rather, a combination of the S and R deflections of the ECG are typically used as diagnostics, for example using the Sokolow-Lyon index, Cornell voltage criteria, or Romhilt-Estes criteria. Another term sometimes used is "Interventricular Conduction Delay" (IVCD), which is diagnosed when the QRS complex duration is greater than 100 milliseconds. BBB is the common source of IVCD, although LVH can also cause such broadening of the QRS complex.

A patient with BBB or LVH is at enhanced risk for a heart attack. Accordingly, rapid and accurate diagnosis of AMI in the presence of BBB or LVH is a critical task for clinical practice.

Detection of acute MI from other confounders, especially BBB and LVH, has long been a challenging issue for ECG diagnosis. Various approaches have been proposed to identify AMI (i.e. STEMI) in the presence of BBB and/or LVH. Typically, these methods examine the amplitude ratio among the ST segment, Q-wave, R-wave or S-wave on each ECG lead. The performance of AMI differentiation tests typically suffers from a trade-off between sensitivity and specificity. For instance, 80% specificity usually accompanies 15% sensitivity in LBBB diagnosis. In other words, for patients with LBBB, most acute MI cannot be identified immediately, leading to delay in AMI treatment and consequent irreversible heart damage or death.

The following discloses a new and improved systems and methods that address the above referenced issues, and others.

In accordance with one aspect, a cardiac monitoring system is disclosed. An electrocardiograph (ECG) monitor is configured for operative connection with a plurality of ECG electrodes. The ECG monitor includes a display device and an electronic data processing component configured to perform ECG analysis of ECG traces for a plurality of ECG leads acquired by the ECG monitor. The ECG analysis includes the operations of determining whether the ECG traces satisfy a set of ST Elevation Myocardial Infarction (STEMI) criteria, and analyzing the ECG traces to detect a confounding cardiac condition that is not AMI but also produces ST deviation. Conditional on the STEMI criteria being satisfied and not detecting the confounding cardiac condition, an AMI alarm is displayed on the display device of the ECG monitor. Conditional on the STEMI criterion being satisfied and also detecting the confounding cardiac condition, the ECG analysis includes the further operations of: converting the ECG traces to a three-dimensional vector cardiograph (3D-VCG) signal; computing an angle between (1) an ST vector characterizing the ST segment of the 3D-VCG signal and (2) a terminal QRS vector characterizing a terminal portion of the QRS complex of the 3D-VCG signal; and conditional on the computed angle being less than a threshold angle, displaying the AMI alarm on the display device of the ECG monitor. The terminal portion of the QRS complex of the 3D-VCG signal may be the last one-third of the QRS complex of the 3D-VCG signal. In a suitable approach, the converting operation comprises converting the ECG traces to said 3D-VCG signal comprising a vector sum of lead vectors in a three-dimensional space wherein each lead vector has magnitude corresponding to a lead voltage and lies along an anatomical direction corresponding to a spatial orientation of the lead voltage. In a case in which the ECG traces are 12-lead ECG traces, the converting operation suitably further comprises calculating the lead voltages comprising Frank lead voltages from the 12-lead ECG traces. The confounding cardiac condition may include one or more of: left bundle branch block (LBBB), right bundle branch block (RBBB), left ventricular hypertrophy (LVH), and Interventricular Conduction Delay (IVCD). In some embodiments the confounding cardiac condition is detected if the QRS complex exceeds a duration threshold. In some more specific embodiments, the ST vector is a vector of the 3D-VCG lying in the ST segment of the 3D-VCG signal (for example, in the middle of the ST segment), and the terminal QRS vector is a vector of the 3D-VCG lying in the terminal portion of the QRS complex of the 3D-VCG signal (for example, the vector of maximum magnitude in the terminal portion of the QRS complex of the 3D-VCG signal). In some more specific embodiments, the threshold angle is in the range [130°, 170°] inclusive.

In accordance with another aspect, a non-transitory storage medium stores instructions readable and executable by an electronic data processing device to perform an electrocardiographic (ECG) monitoring method operating on ECG traces acquired from a subject using a plurality of ECG leads. The ECG monitoring method comprises determining whether the subject has acute myocardial infarction (AMI) by determining whether one of the following is satisfied: (1) the ECG traces satisfy an ST Elevation Myocardial Infarction (STEMI) criterion and the ECG traces do not indicate the subject has a confounding cardiac condition that is not AMI and that produces ST elevation, or (2) the ECG traces satisfy the STEMI criterion and the ECG traces also indicate the subject has the confounding cardiac condition and a three-dimensional vector cardiograph (3D-VCG) signal generated from the ECG traces acquired from the subject includes an ST vector in the ST segment of the 3D-VCG signal and a terminal QRS vector of maximum magnitude in a terminal portion of the QRS complex of the 3D-VCG signal for which the angle between the ST vector and the terminal QRS vector is less than a threshold angle. The ECG monitoring method may further comprise outputting a human-perceptible AMI alarm in response to determining the subject has AMI. In some embodiments the threshold angle is in the range [130°, 170°] inclusive. The 3D-VCG signal is suitably a vector sum of ECG lead vectors in a three-dimensional space. In some embodiments the confounding cardiac condition includes both left bundle branch block (LBBB) and left ventricular hypertrophy (LVH). In some embodiments the confounding cardiac condition includes Interventricular Conduction Delay (IVCD) indicated by the QRS complex having duration longer than a threshold duration wherein the duration threshold is at least 100 milliseconds.

In accordance with another aspect, a non-transitory storage medium stores instructions readable and executable by an electronic data processing device to perform an electrocardiographic (ECG) monitoring method operating on ECG traces acquired from a subject using a plurality of ECG leads. The ECG monitoring method comprises determining whether the subject has acute myocardial infarction (AMI) by determining whether: (i) the ECG traces satisfy an ST Elevation Myocardial Infarction (STEMI) criterion and (ii) the ECG traces also indicate the subject has the confounding cardiac condition and (iii) a vector angle difference between an ST vector in the ST segment and a terminal QRS vector of maximum magnitude in a terminal portion of the QRS complex is less than a threshold angle wherein the ST vector and the terminal QRS vector reside in a three-dimensional space defined by an orthogonal set of basis vectors generated from the ECG traces acquired from the subject. The ECG monitoring method further comprises outputting a human-perceptible AMI alarm in response to determining the subject has AMI.

In accordance with another aspect, a method is disclosed for determining acute myocardial infarction (AMI). The method comprises: obtaining ECG traces from a subject; identifying a deviation of the ST portion of the ECG traces; converting the ECG traces into a three-dimensional vector cardiogram (3D VCG) signal having a QRS vector and an ST vector; calculating a vector angle between the QRS vector and the ST vector; and classifying the subject as AMI or non-AMI based upon the calculated vector angle. In some more specific embodiments, the ST vector corresponds to a middle segment of the single ST portion of the 3D-VCG, and/or the QRS vector corresponds to a terminal part of the QRS portion of the 3D-VCG, such as the vector of maximum voltage magnitude in the terminal part of the QRS portion of the 3D-VGC. In a specific embodiment, the classification step classifies the subject as AMI if the calculated vector angle is less than 150 degrees, and if otherwise, classifies the subject as non-AMI.

One advantage resides in improved detection of acute myocardial infarction (AMI) by electrocardiography (ECG) in the presence of confounding conditions such as bundle branch block (BBB), left ventricular hypertrophy (LVH), and/or Interventricular Conduction Delay (IVCD).

Another advantage resides in improved sensitivity in detection of AMI by ECG in the presence of confounding conditions.

Another advantage resides in improved specificity in detection of AMI by ECG in the presence of confounding conditions.

Still further advantages will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

It is recognized herein that the hard trade-off between sensitivity and specificity in AMI differentiation tests is that all these methods are based on observation on each individual ECG lead (or channel). The myocardial electrical activity represented by a single ECG lead constitutes a spatial projection of the three-dimensional cardiac activity, and exhibits waveform instability due to the deviations in anatomy from patient-to-patient and over time for a single patient, as well as deviations in electrode location from patient to patient. Disclosed herein are improved AMI differentiation tests that operate on relative vector comparisons (e.g. angles between vectors, vector magnitude ratios) of vector features computed in a three-dimensional vector cardiograph (3D-VCG) space. In the 3D-VCG space, deviations in anatomy and electrode placement translate into small-angle rotations or other small deviations or distortions in the three-dimensional space. As a consequence, instability is substantially reduced and so both sensitivity and specificity are improved. The disclosed approaches also have intuitive interpretation which assists physicians in diagnosis, and are readily implemented in a multi-leads diagnostic ECG acquisition/analysis system.

Figure 1:
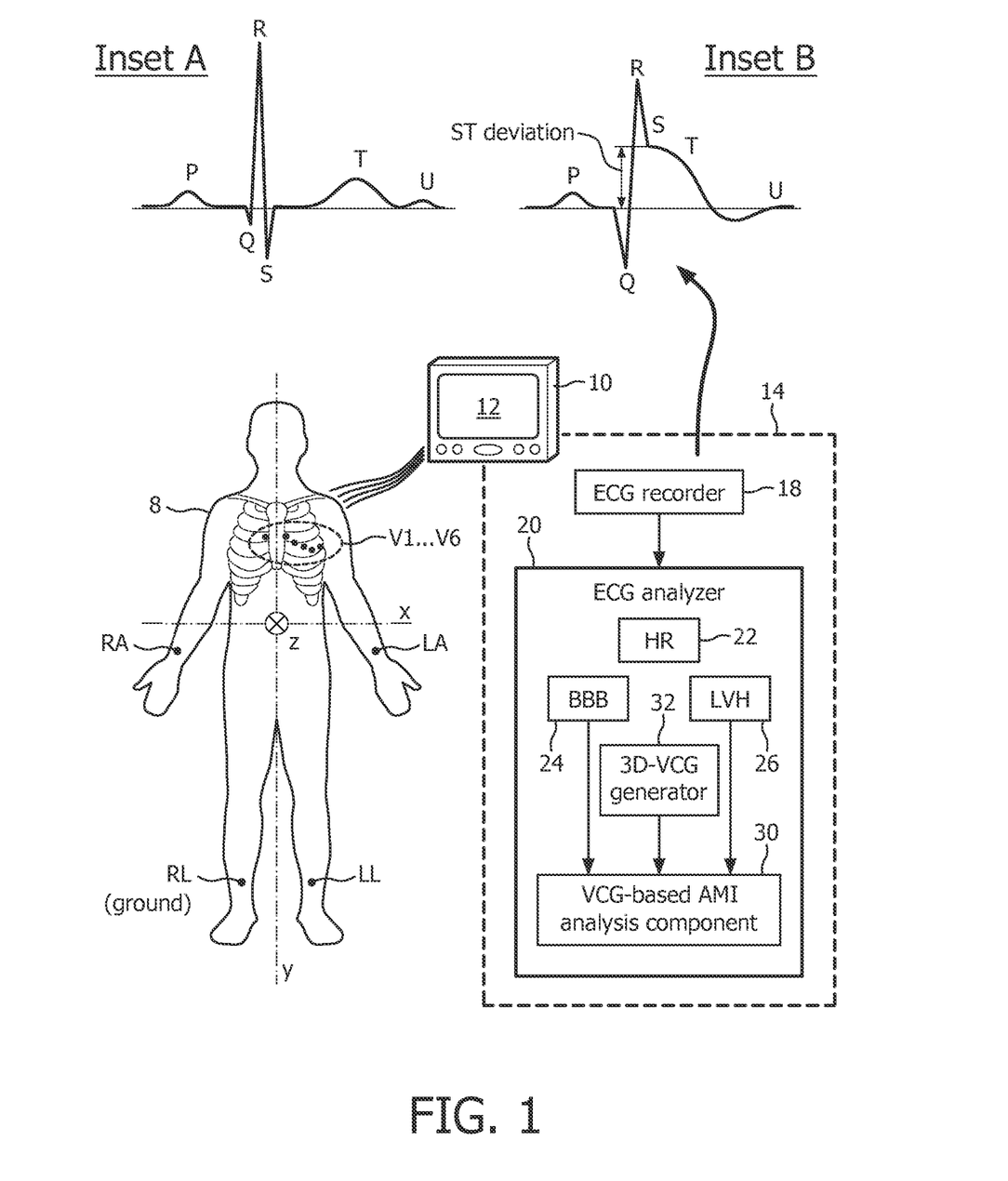
FIG. 1 diagrammatically illustrates an electrocardiograph (ECG)-based patient monitoring and cardiac diagnosis system configured to differentiate acute myocardial infarction (AMI) from confounding conditions including bundle branch block (BBB) and left ventricular hypertrophy (LVH).

With reference to FIG. 1, a subject 8 (e.g. a hospital patient, a patient at an emergency medical facility, a patient visiting his or her physician for a physical, a cardiac screening subject, or so forth) is connected with an electrocardiograph (ECG) monitor 10 by ECG electrodes. The illustrative embodiment employs a conventional 12-lead ECG in which six chest electrodes V1, . . . , V6 are connected to the chest, a left arm electrode LA is connected to the left arm, a right arm electrode RA is connected to the right arm, and a left leg electrode LL is connected to the left leg. A ground electrode is also connected, in the illustrative example as a right leg electrode RL. Voltages between defined pairs of these electrodes define the various leads (or channels) of the 12-lead ECG, as presented in Table 1.

TABLE 1

Standard 12-Lead ECG

| Lead | Type | Lead Calculation |
|---|---|---|
| I | Limb | LA − RA |
| II | Limb | LL − RA |
| III | Limb | LL − LA |
| AVR | Augmented | RA − (LA + LL)/2 |
| AVL | Augmented | LA − (RA + LL)/2 |
| AVF | Augmented | LL − (RA + LA)/2 |
| V1 | Precordial | V1 − (RA + LA + LL)/3 |
| V2 | Precordial | V2 − (RA + LA + LL)/3 |
| V3 | Precordial | V3 − (RA + LA + LL)/3 |
| V4 | Precordial | V4 − (RA + LA + LL)/3 |
| V5 | Precordial | V5 − (RA + LA + LL)/3 |
| V6 | Precordial | V6 − (RA + LA + LL)/3 |

While the illustrative 12-lead ECG is a standard ECG configuration, various modified electrode configurations may alternatively be employed, such as the Mason-Likar ECG in which the limb electrodes are moved off the limbs toward the body center-of-mass, e.g. onto the torso, or a reduced-electrodes configuration such as the EASI system (where the leads of the 12-lead ECG can be computed using suitable mathematical transforms). It will also be appreciated that electrode placement onto the subject 8 is generally a manual process and the precise electrode positions will vary from subject to subject due to individual differences in subject anatomy, individual differences in the medical caregiver's expertise in electrode placement, and so forth.

The ECG monitor 10 includes a display device 12 on which acquired ECG data and information derived from ECG analysis are displayed. The display device 12 may be a liquid crystal display (LCD) display device, a plasma display device, an organic light emitting diode (OLED) display device, or so forth. The ECG monitor 10 further includes an electronic data processing component 14 which is diagrammatically represented in FIG. 1 by a dashed box. The electronic data processing component 14 may, for example, comprise an electronic microprocessor or microcontroller and ancillary components such as operatively connected read-only memory (ROM) and/or random access memory (RAM) and/or flash memory and/or hard disk drive and/or optical disk drive, et cetera, storing instructions executable by the microprocessor or microcontroller to perform ECG-related functions including implementing an ECG recorder 18 and an ECG analyzer 20. The electronic data processing component 14 is also operatively connected with the display device 12 to display ECG lead traces, ECG analysis results such as the heart rate (HR), and so forth. It will also be appreciated that the ECG analyzer 20 may be embodied as a non-transitory storage medium storing instructions readable and executable by an electronic data processing device (such as the electronic data processing component 14 of the ECG monitor 10) to perform the ECG analyses performed by the ECG analyzer 20. The non-transitory storage medium may, for example, comprise a hard disk drive or other magnetic storage medium, a flash memory, read-only memory (ROM), electronically programmable read-only memory (EPROM), or other electronic storage medium, an optical disk or other optical storage medium, various combinations thereof, or so forth.

In some embodiments the ECG monitor 10 may comprise a multi-parameter physiological monitor that monitors ECG as well as other physiological parameters such as blood pressure via a blood pressure sensor, peripheral capillary oxygen saturation (SpO$_2$) via a SpO$_2$ sensor, respiration rate via a respiratory sensor, or so forth.

The ECG recorder 18 records voltage samples as a function of time for each lead of the 12-lead ECG. To this end, the ECG recorder 18 acquires the potentials on the two electrodes of the lead (for example, electrodes LA and RA for Lead I) for each time interval and computes the lead voltage for the time interval as the difference (e.g. the voltage of Lead I equals LA-RA). In an Inset A of FIG. 1, a typical ECG trace for Lead II for a subject with a healthy heart is diagrammatically shown over one cardiac cycle (i.e. one heart beat). This typical ECG trace includes features (also called "waves") labeled as P, QRS, T, and U according to convention. The P-wave represents the depolarization and contraction of both atria, the QRS complex represents the depolarization and contraction of the ventricles, and the T-wave represents the repolarization of the ventricles. After ventricular depolarization, normal myocardial cells are at nearly the same potential. Therefore in the absence of any cardiac pathology, the end of depolarization (that is, the termination of the QRS complex, also called the "J-point") and the beginning of repolarization (that is, the beginning of the T-wave) are normally isoelectric. In the ECG, this region is called the ST segment, and is nearly flat and at nearly zero potential for a normal, healthy heart. The ECG traces for other leads follow similar patterns, but with differences in wave amplitudes and/or polarities and/or widths and/or detailed shapes.

In an Inset B of FIG. 1, the corresponding ECG trace for a subject in acute myocardial infarction (AMI) is shown. A principal observed difference as compared with the "normal" ECG trace of Inset A is that the ST segment is elevated—that is, the ST segment has a positive "ST deviation" as indicated in Inset B. The ST deviation is conventionally reported in millivolts (mV) or millimeters (mm), the latter assuming that 1 mm corresponds to 0.1 mV. An elevated ST level (i.e. a positive ST deviation) is an indicator of AMI. Depending upon the specific STEMI criteria being applied and factors such as the particular lead under consideration and the gender of the subject 8, an ST elevation of greater than 0.15 mV to 0.2 mV is considered diagnostic of AMI.

Figure 2:
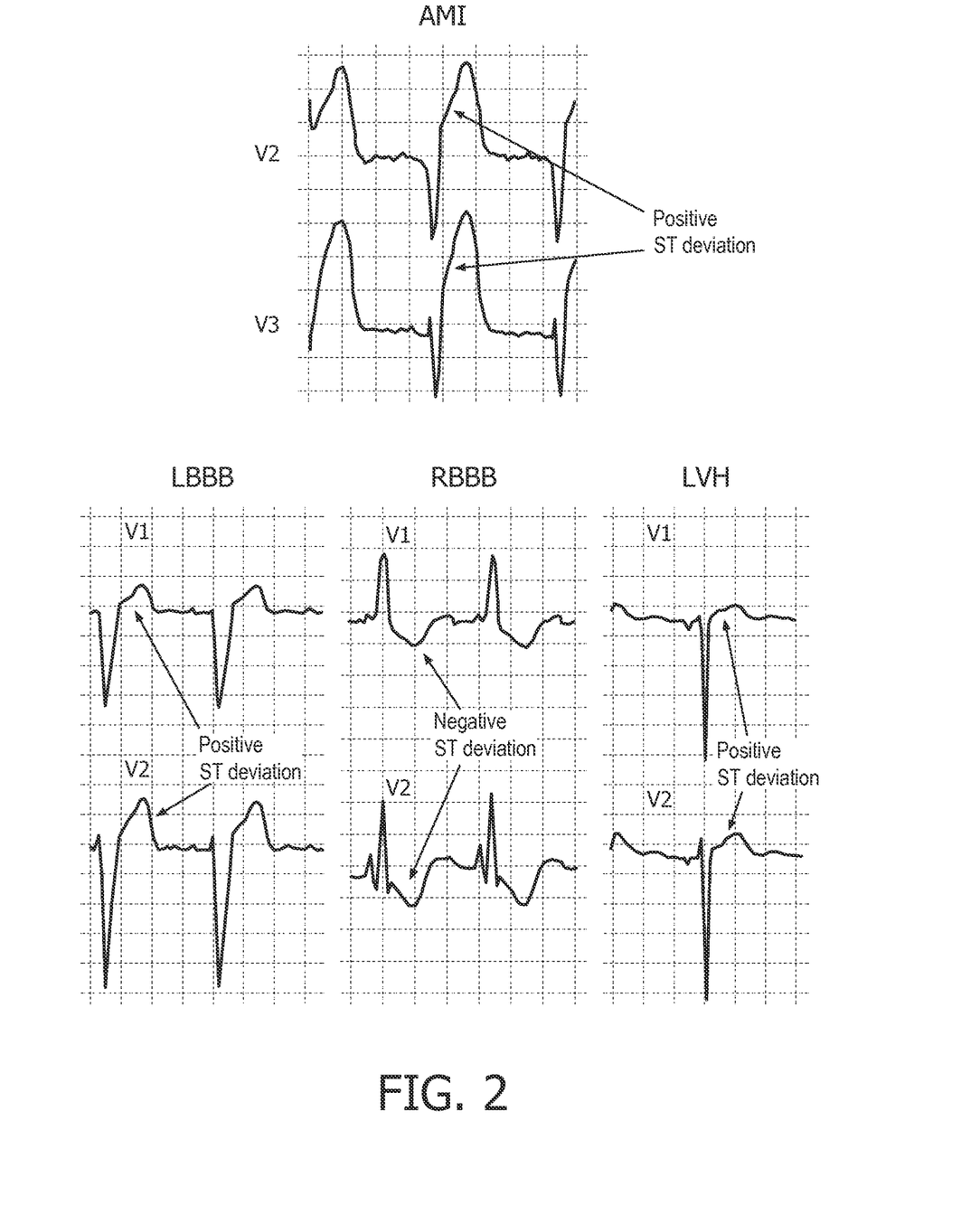
FIG. 2 diagrammatically illustrates typical ECG traces in the presence of AMI, left bundle branch block (LBBB), right bundle branch block (RBBB), and LVH.

With continuing reference to FIG. 1 and with further reference to FIG. 2, this AMI diagnostic can be confounded by other conditions, such as LBBB or LVH, that also produce ST elevation. As shown in FIG. 2, each of the AMI, LBBB, and LVH conditions produce ST elevation (that is, a positive ST deviation). RBBB, on the other hand, produces ST depression (that is, a negative ST deviation). These confounding conditions complicate interpretation of the ECG for diagnosing AMI.

With continuing reference to FIG. 1, the ECG analyzer 20 performs ECG analysis including differentiation of AMI from confounding BBB and/or LVH conditions. The illustrative ECG analyzer 20 includes a heart rate (HR) analysis component 22 that computes heart rate from the periodicity of the ECG trace. Various approaches can be used, such as measuring the R-wave separation in successive cardiac cycles. A bundle branch block (BBB) analysis component 24 analyzes the ECG to detect BBB and, if detected, to differentiate between left bundle branch block (LBBB) and right bundle branch block (RBBB). In one suitable approach, BBB is diagnosed if the QRS complex is broader than some threshold (which may be a function of heart rate as this affects the total duration of one cardiac cycle). The detailed shape of the QRS complex is analyzed to differentiate between LBBB and RBBB. Features of other waves, such as the T wave, may also be used in the ECG analysis to diagnose BBB. A left ventricular hypertrophy (LVH) analysis component 26 analyzes the ECG to detect LVH, for example based on a combination of the S and R points of the ECG using the Sokolow-Lyon index, Cornell voltage criteria, Romhilt-Estes system, or another suitable LVH diagnostic criterion. Although not illustrated, the ECG analyzer 20 may include other analysis components for diagnosing other cardiac conditions.

Figure 3:
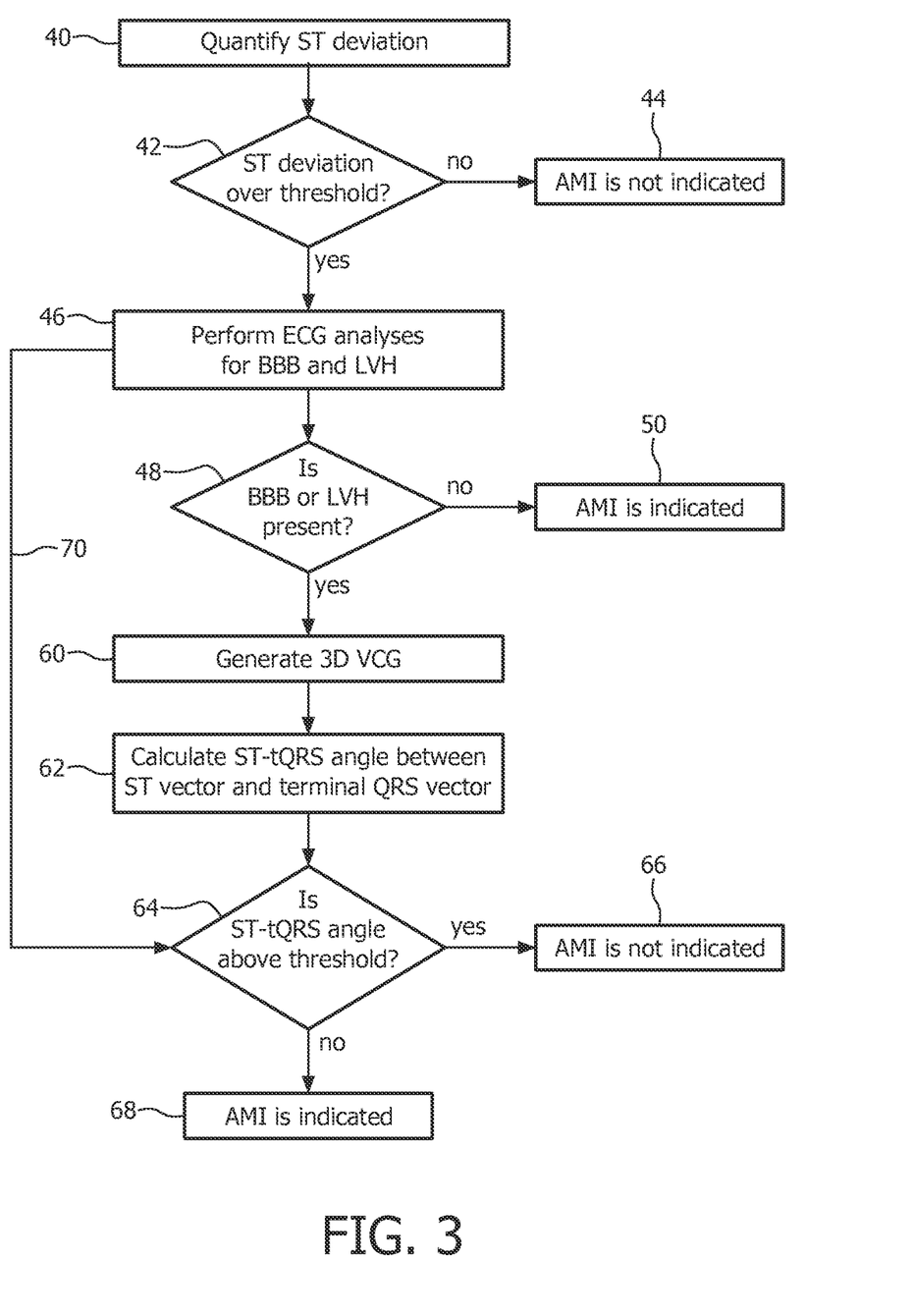
FIG. 3 diagrammatically illustrates a suitable method performed by the ECG analyzer of the system of FIG. 1.

With continuing reference to FIG. 1 and with further reference to FIG. 3, an AMI analysis component 30 analyzes the ECG to detect acute myocardial infarction (AMI). Where appropriate, the AMI analysis performed by the AMI analysis module 30 includes differentiating AMI from confounding BBB and/or LVH conditions by a vector analysis performed on a three-dimensional vector cardiograph (3D-VCG), in a VGC space, computed from the ECG data by a 3D-VCG generator 32. FIG. 3 diagrammatically shows an illustrative AMI diagnostic process suitably performed by the components 30, 32. In an operation 40, the ST segment deviation is quantified in one, two, several, or all ECG lead traces, and in an operation 42 the ST segment deviation in the one or more leads is compared with thresholds in accordance with a STEMI criterion to determine whether the ST deviation is indicative of AMI. Various STEMI criteria have been promulgated in the relevant medical literature, and may be used in the operation 42. In one suitable STEMI criterion, AMI is diagnosed if (in the absence of QRS confounders) an ST elevation at the J point observed in two contiguous leads is greater than or equal to 0.2 mV (for men) or 0.15 mV (for women) in leads V2-V3 and/or 0.1 mV in other leads. Alpert et al., "The universal definition of myocardial infarction: a consensus document: Ischaemic heart disease", *Heart* vol. 94 pages 1335-41 (2008). If the STEMI criteria are not met in the operation 42, then it is concluded in an operation 44 that AMI is not indicated.

The STEMI criteria applied in the operation 42 are appropriate in the absence of QRS confounders. Alpert et al., supra. Accordingly, if in the operation 42 it is found that the STEMI criteria are met, it cannot be immediately concluded that AMI is indicated—rather, the elevated ST segment could be due to a confounding condition such as LBBB or LVH. Accordingly, in an operation 46 the ECG analyses to detect BBB and LVH are performed, for example by the BBB and LVH analysis components 24, 26 as already described. In an operation 48, the outputs of the BBB and LVH analysis components 24, 26 are inspected to determine whether the subject 8 is diagnosed with either BBB or LVH. If the operation 48 concludes that neither BBB nor LVH is present, then there are no confounding conditions and it is concluded in an operation 50 that AMI is indicated.

On the other hand, if the operation 48 indicates that either BBB or LVH, or both, are diagnosed in the subject 8, then there is the possibility that the positive result for the STEMI criterion in the operation 42 is actually due to the confounding condition, rather than being due to AMI. In this case, the AMI analysis component 30 proceeds with the VCG-based AMI differentiation process. To this end, in an operation 60 the 3D-VCG generator 32 is invoked to convert the ECG signals from the leads of the 12-lead ECG to a 3D-VCG signal. Vector cardiography (VCG) describes the electrical activity of the heart as an ECG vector (as a function of time) in a three-dimensional VCG space. See, e.g. Robert B. Northrup, NONINVASIVE INSTRUMENTATION AND MEASUREMENT IN MEDICAL DIAGNOSIS (CRC Press 2002) chapter 4. In a conventional VCG coordinate system for the human anatomy, the x-axis runs horizontally from the right hand to the left hand through the chest, the y-axis runs vertically from head to feet, and the z-axis runs from the chest to the back. In FIG. 1, these x, y, z axes are diagrammatically shown superimposed on the subject 8 using dashed axis lines (with the z axis perpendicular to the paper). In this coordinate system, the sagittal (or median) plane is the y-z plane passing vertically through the center of the body, the coronal (or horizontal) plane is the x-z plane, and the frontal plane is the x-y plane. The ECG vector of the 3D-VCG is defined in the VCG coordinate system as a vector sum of component (or lead) vectors in the three-dimensional VCG space with each component (lead) vector having magnitude corresponding to a lead voltage and lying along an anatomical direction corresponding to the spatial orientation of the lead voltage. It will be appreciated that small errors in positioning of the electrodes on the subject 8 will merely result in slight deviation of the corresponding lead vector in the VCG space and consequent slight distortion of the 3D-VCG signal. The summation of the constituent ECG lead vectors to generate the 3D-VCG signal can employ various mathematical approaches. In a suitable approach for generating the 3D-VCG signal, the three-dimensional VCG signal is calculated from standard 12-lead ECG by the EASI coefficient transform to Frank leads so as to resolve the three orthogonal components of the 3D-VCG signal.

Based on clinical observations, it has been determined that AMI can be differentiated from BBB and LVH based on comparison of the ST vector, denoted herein as ST, and the terminal (or end) QRS vector, denoted herein as tQRS. These vectors can be compared in terms of the angle between them, denoted herein as $\angle$ (ST-tQRS). These vectors can additionally or alternatively be compared in terms of their magnitude ratio, denoted herein as (|ST|/|tQRS|). In the ECG trace of a subject with a healthy heart, the ST segment is substantially flat (see FIG. 1, Inset A); however, in the case of an ST segment deviation due to a cardiac pathology, the ST segment can have substantial curvature (see FIG. 1, Inset B and FIG. 2). Accordingly, the vector ST should be defined in some standard way. In the illustrative embodiments, the vector ST is defined as the middle vector of the ST segment—that is, the vector at the point halfway between the S and T points. The termination or end of the QRS segment also should be defined in a standard way. In the illustrative embodiments, the terminal QRS vector (tQRS) is defined as the vector of maximum magnitude in a terminal portion (e.g. the last one-third) of the QRS segment of the VCG signal generated from the acquired ECG traces. Other standard definitions for the ST and terminal QRS vectors are contemplated. More generally, an ST vector is defined that characterizes the ST segment of the 3D-VCG signal, and a QRS vector is defined that characterizes the QRS complex of the 3D-VCG signal.

Based on clinical observations, it has been found that the angle $\angle$ (ST-tQRS) is especially useful for differentiating AMI from confounding BBB and/or LVH conditions. Using the aforedescribed illustrative definitions of the ST and tQRS vectors, it was found that an effective test for differentiating AMI is as follows: If $\angle$ (ST-tQRS)>150° then the ST segment deviation is not due to AMI; whereas, if $\angle$ (ST-tQRS)≤150° then the ST segment deviation is due to AMI. While an AMI/confounder differentiation threshold of 150° (that is, 150 degrees) is used in these examples, it will be appreciated that the precise threshold may be adjusted to achieve a desired trade-off between sensitivity and specificity. Additionally, if the ST and/or tQRS vectors are defined differently, then the threshold may need to be adjusted accordingly. Thus, more generally the AMI differentiation test can be stated as:

If $\angle(\text{ST-tQRS}) > \angle \text{Th}$ then AMI is not indicated

If $\angle(\text{ST-tQRS}) \leq \angle \text{Th}$ then AMI is indicated where $\angle \text{Th}$ is a threshold angle, e.g. $\angle \text{Th}=150°$ in the illustrative embodiments. In general, increasing threshold $\angle \text{Th}$ provides a higher likelihood of the test indicating AMI (that is, higher sensitivity, i.e. reduced likelihood of missing an actual AMI case). On the other hand, decreasing the threshold $\angle \text{Th}$ provides a lower likelihood of the test indicating AMI (that is, higher specificity, i.e. reduced likelihood of misdiagnosing a case which is not AMI as AMI). For the conventional VCG space of FIG. 1, clinical observations indicate that a suitable range for the threshold $\angle \text{Th}$ is in the range [130°, 170°] inclusive (that is, including the end-points 130° and 170°), although setting $\angle \text{Th}$ below 130° or above 170° is also contemplated.

In another variant AMI test, it is contemplated to employ different thresholds for differentiating AMI from BBB and LVH, respectively. The AMI differentiation test in this case becomes:

If BBB and $\angle(\text{ST-tQRS}) > \angle \text{Th}_{BBB}$ then AMI is not indicated If BBB and $\angle(\text{ST-tQRS}) \leq \angle \text{Th}_{BBB}$ then AMI is indicated If LVH and $\angle(\text{ST-tQRS}) > \angle \text{Th}_{LVH}$ then AMI is not indicated If LVH and $\angle(\text{ST-tQRS}) \leq \angle \text{Th}_{LVH}$ then AMI is indicated In one suitable embodiment, $\angle \text{Th}_{BBB}=130°$ and $\angle \text{Th}_{LVH}=170°$, although other threshold values are contemplated to achieve desired sensitivity and specificity, or to accommodate different VCG systems, or so forth. (There may be an ambiguity if both BBB and LVH are present—in this case, given the acute nature of AMI it is generally preferable to indicate AMI if $\angle(\text{ST-tQRS})$ is less than either of the two angles $\angle \text{Th}_{BBB}$, $\angle \text{Th}_{LVH}$).

Thus, with returning reference to FIGS. 1 and 3, in an operation 62 the AMI analysis component 30 computes the angle between the vectors ST and tQRS, that is, computes the angle $\angle(\text{ST-tQRS})$. In an operation 64, the AMI analysis component 30 compares this angle against the threshold angle $\angle \text{Th}$. If $\angle(\text{ST-tQRS}) > \angle \text{Th}$ then in an operation 66 it is concluded that AMI is not indicated; otherwise, in an operation 68 is it concluded that AMI is indicated. (In the variant embodiment in which different thresholds $\angle \text{Th}_{BBB}$ and $\angle \text{Th}_{LVH}$ are used, the appropriate threshold for use in operation 64 is selected based on the output of the BBB and LVH tests performed in the operation 46, as indicated by the data flow arrow 70 in FIG. 3). and If AMI is indicated, then the ECG monitor 10 provides a suitable human-perceptible indication of possible AMI in the subject 8, such as displaying a suitable text message on the display device 12, possibly highlighted by flashing, a distinctive font (e.g. red) and/or a distinctive background color, or so forth. The human-perceptible indication of possible AMI in the subject 8 optionally also includes an audible indication, such as generating an audio alarm using a speaker (not shown) of the ECG monitor 10.

While the AMI analysis component 30 differentiates AMI from confounding BBB and LVH conditions, this does not preclude the possibility that the subject 8 may have some combination of AMI, BBB, and LVH. Indeed, if the AMI analysis process of FIG. 3 reaches operation 60 then the subject 8 is diagnosed as having BBB and/or LVH, in accord with the result of operation 46. In the illustrative configuration of the ECG monitor 10 of FIG. 1, providing a human-perceptible indication of any diagnosed BBB condition is handled by the BBB analysis component 24, while providing a human-perceptible indication of any diagnosed LVH condition is handled by the LVH analysis component 26. However, integrated configurations are also contemplated—for example the BBB and LVH components 24, 26 may be integrated with the component 30. From a clinical perspective, however, AMI is a more critical condition than either BBB or LVH, and accordingly if the AMI is diagnosed in combination with either BBB or LVH (or both) then the ECG monitor is preferably configured to emphasize the AMI alarm over the BBB or LVH alarm, or may be configured to suppress the BBB or LVH alarm entirely if AMI is diagnosed.

The AMI test described with reference to FIG. 3 relies upon the ECG monitor 10 providing the BBB and LVH tests 24, 26 in order to perform the operation 46. In an alternative embodiment, the operation 46 tests for Interventricular Conduction Delay (IVCD), for example diagnosing IVCD if the QRS complex duration is greater than 100 milliseconds (or some other threshold, e.g. 130 milliseconds in some embodiments). IVCD is a suitable surrogate for BBB and, to a lesser extent, for LVH. In this variant AMI test, the operation 48 then determines whether IVCD is present based on the test run in the (modified) operation 46: If IVCD is not present then AMI is indicates as per operation 50; if IVCD is present then processing flows to operation 60 to generate the 3D-VCG signal which is then analyzed as previously described. Thus, this variant AMI test can be performed without leveraging the BBB and LVH tests 24, 26.

The disclosed AMI differentiation tests are based on comparison of vectors (e.g. angle between the vectors) of the 3D-VCG signal generated from the ECG traces. Because of this, the choice of VCG coordinate system is arbitrary, e.g. while in illustrative FIG. 1 the x, y, and z axes are as indicated, in other embodiments the x-axis may be designated as the axis running vertically from head to feet, et cetera. The component (i.e. lead) vectors are preferably defined in the VCG space to generally correspond to the physical directions of the corresponding ECG voltage measurements (which in turn are defined by the positions of the electrodes used to measure the lead voltage), but exact correspondence between the physical voltage orientation and the corresponding component vector direction in VCG space is not necessary. Differences between the physical voltage orientation and the corresponding component vector direction in the VCG space are suitably accommodated by adjustment of the threshold $\angle \text{Th}$ based on a training set of clinical observations converted to the chosen VCG space.

Figure 4:
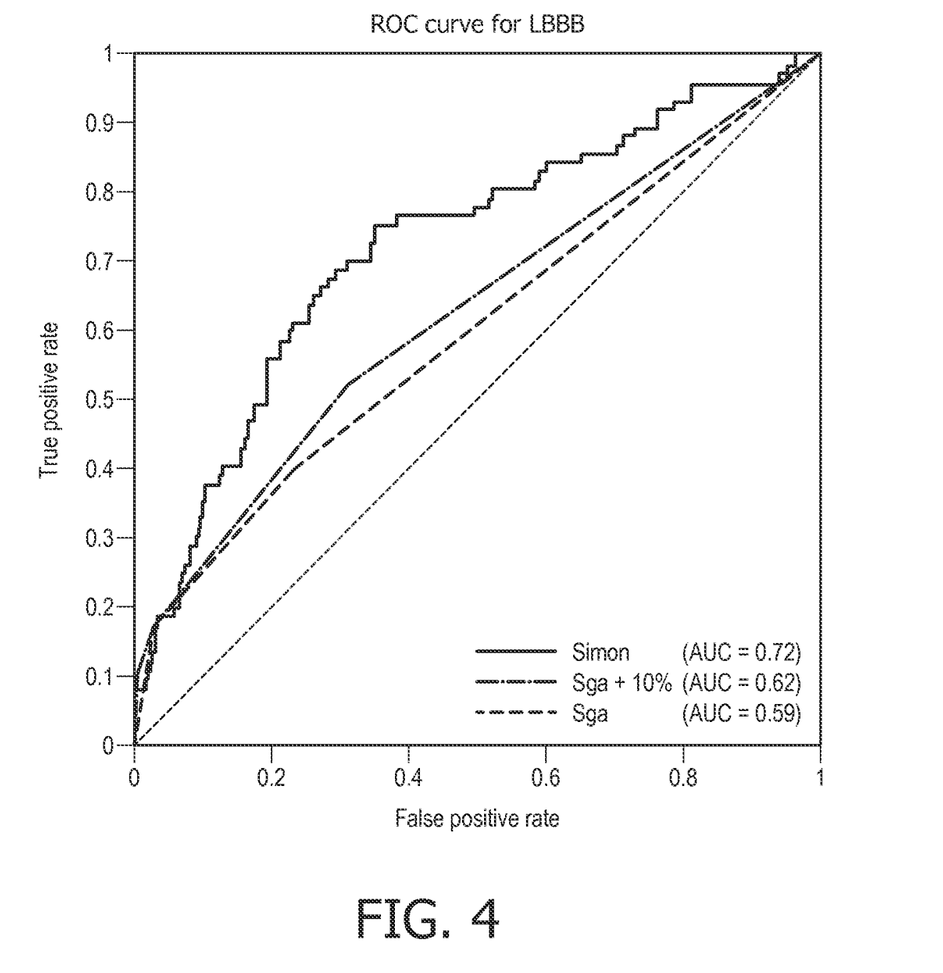
FIGS. 4-6 present Receiver Operating Curve (ROC) plots for the disclosed AMI differentiation test as described herein.
Figure 5:
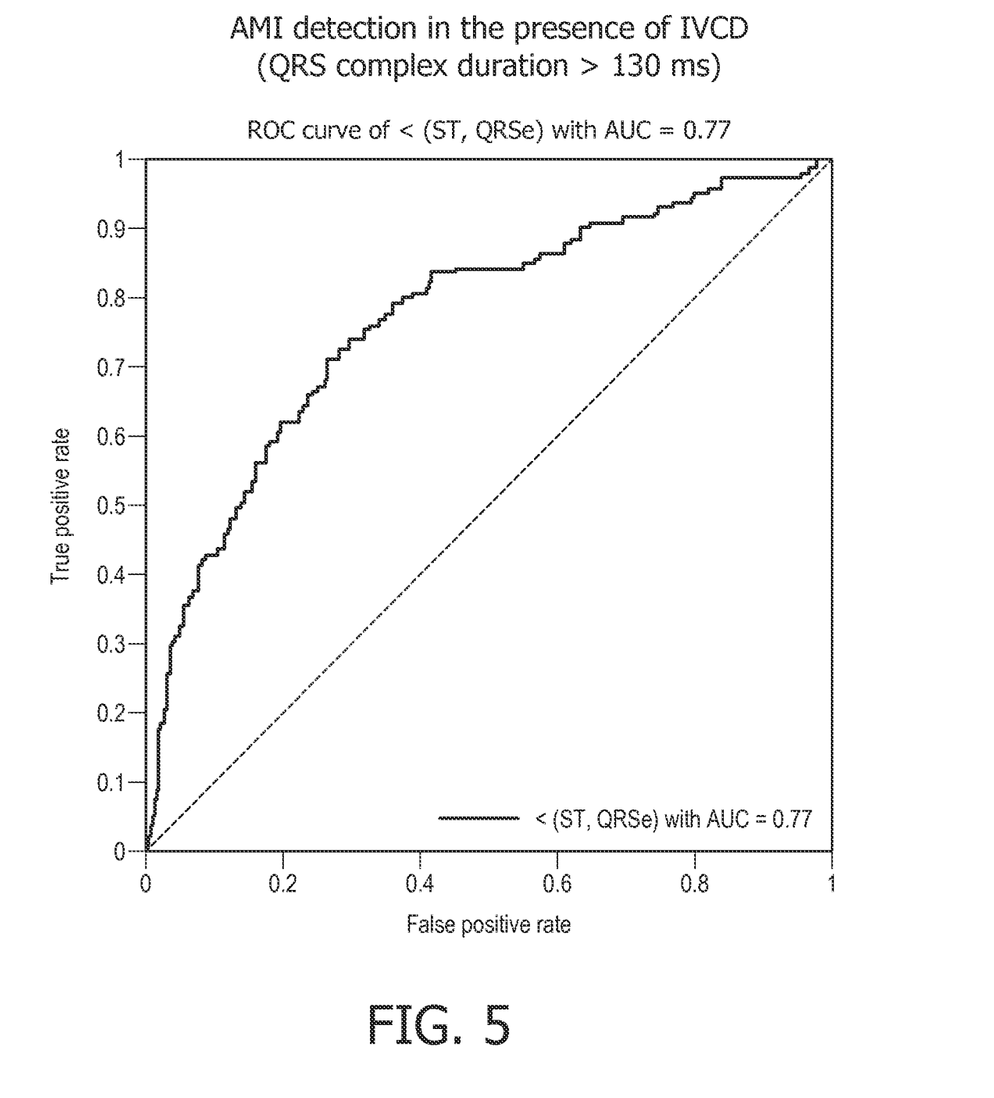
Figure 6:
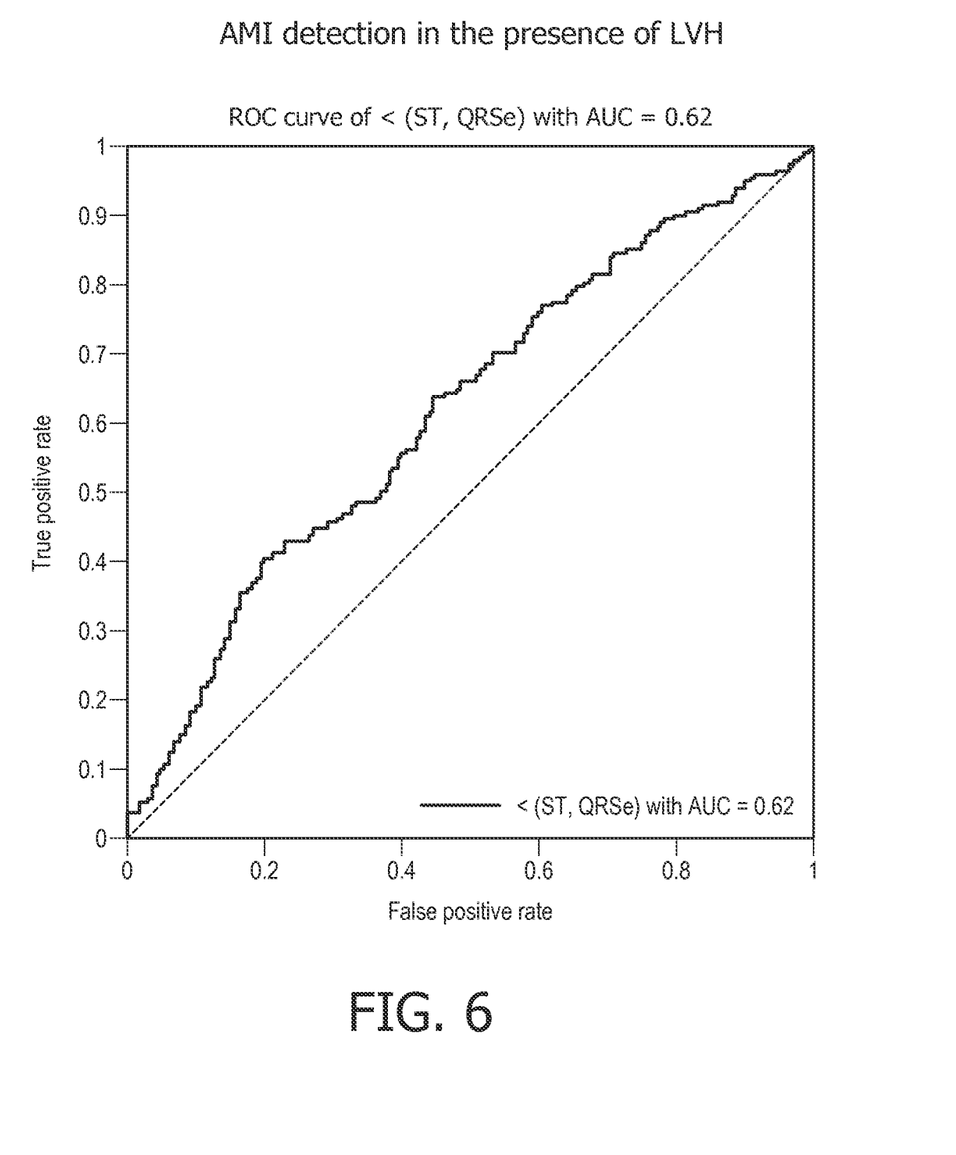

With reference to FIGS. 4-6, Receiver Operating Curve (ROC) plots are presented illustrating efficacy of the disclosed AMI differentiation approaches. In each ROC, the dashed line oriented at 45° represents a test with Area Under Curve (AUC) of 0.5 corresponding to the results of a "random guessing" test.

The ROC of FIG. 4 compares AMI detection in the presence of LBBB using the approach disclosed herein (labeled "Simon" in FIG. 4 and having AUC=0.72) with two tests from the literature: the "Sga" test having AUC=0.59 described in Sgarbossa et al., "Electrocardiographic Diagnosis of Evolving Acute Myocardial Infarction in the presence of Left Bundle-Branch Block", The New England Journal of Medicine vol. 334 no. 8 pp. 481-487 (1996); and "Sga+10%" test having AUC=0.62, which is a variant of the SGA test.

The ROC of FIG. 5 shows AMI detection in the presence of IVCD (defined here as a QRS complex duration of greater than 130 milliseconds) using the approach disclosed herein. The AUC is 0.77.

The ROC of FIG. 6 shows AMI detection in the presence of LVH using the approach disclosed herein. The AUC is 0.62.

In the illustrative embodiments, the ST vector characterizing the ST segment and the terminal QRS vector characterizing the terminal portion of the QRS complex are defined in a 3D-VCG space. However, these vectors may more generally reside in a three-dimensional space defined by an orthogonal set of basis vectors generated from the ECG traces acquired from the subject. For example, in another embodiment, the anatomical directions are determined by the voltage differences between different leads of the 12-lead ECG. Differences in anatomical direction of the terminal portion of the QRS and the anatomical direction of the ST segment then direct the AMI decision. Another example method for determining direction vector differences between the ST segment and terminal QRS is to use the first three principal components of the ECG signal derived from 12-lead ECG. The first three principal components suitably form a set of orthogonal basis functions. For instance, principal component analysis (PCA) can be used to calculate eigenvalues and eigenvectors (which may be approximate or "pseudo"-eigenvalues and "pseudo"-eigenvectors, depending upon the type of PCA employed) from the 12 leads of the 12-lead ECG. The first three principal components (eigenvectors) make up an orthogonal set of basis functions as the Frank X, Y and Z are orthogonal. Those three principal components can be used in place of Frank X, Y and Z to calculate vector angle differences and vector magnitude differences.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A cardiac monitoring system comprising:
an electrocardiograph (ECG) monitor configured for operative connection with a plurality of ECG electrodes, the ECG monitor including a display device and an electronic data processing component configured to perform ECG analysis of ECG traces for a plurality of ECG leads acquired by the ECG monitor including the operations of:
determining whether the ECG traces satisfy an ST Elevation Myocardial Infarction (STEMI) criterion;
analyzing the ECG traces to detect a confounding cardiac condition that is not acute myocardial infarction (AMI) and that produces ST deviation;
conditional on the STEMI criterion being satisfied and not detecting the confounding cardiac condition, displaying an AMI alarm on the display device of the ECG monitor;
conditional on the STEMI criterion being satisfied and also detecting the confounding cardiac condition, performing the further operations of:
converting the ECG traces to a three-dimensional vector cardiograph (3D-VCG) signal;
computing an angle between (1) an ST vector characterizing the ST segment of the 3D-VCG signal and (2) a terminal QRS vector characterizing a terminal portion of the QRS complex of the 3D-VCG signal; and
conditional on the computed angle being less than a threshold angle, displaying the AMI alarm on the display device of the ECG monitor.

2. The cardiac monitoring system of claim 1 wherein the converting operation comprises:
converting the ECG traces to said 3D-VCG signal comprising a vector sum of lead vectors in a three-dimensional space wherein each lead vector has magnitude corresponding to a lead voltage and lies along an anatomical direction corresponding to a spatial orientation of the lead voltage.

3. The cardiac monitoring system of claim 2 wherein the ECG traces for the plurality of ECG leads acquired by the ECG monitor are 12-lead ECG traces and the converting operation further comprises:
calculating the lead voltages comprising Frank lead voltages from the 12-lead ECG traces.

4. The cardiac monitoring system of claim 1 wherein the confounding cardiac condition includes one or more of: left bundle branch block (LBBB), right bundle branch block (RBBB), left ventricular hypertrophy (LVH), and Interventricular Conduction Delay (IVCD).

5. The cardiac monitoring system of claim 1 wherein the operation of analyzing the ECG traces to detect the confounding cardiac condition comprises:
detecting the confounding cardiac condition if the QRS complex exceeds a threshold duration.

6. The cardiac monitoring system of claim 1 wherein:
the operation of analyzing the ECG traces to detect the confounding cardiac condition includes analyzing the ECG traces to detect a bundle branch block (BBB) condition and analyzing the ECG traces to detect a left ventricular hypertrophy (LVH) condition; and
the AMI alarm is displayed on the display device of the ECG monitor conditional on the computed angle being less than (i) a threshold angle $\angle \text{Th}_{BBB}$ if BBB is detected or (ii) a threshold angle $\angle \text{Th}_{LVH}$ if LVH is detected.

7. The cardiac monitoring system of claim 1 wherein:
the ST vector is a vector of the 3D-VCG lying in the ST segment of the 3D-VCG signal; and
the terminal QRS vector is a vector of the 3D-VCG lying in the terminal portion of the QRS complex of the 3D-VCG signal.

8. The cardiac monitoring system of claim 1 wherein:
the ST vector is the vector of the 3D-VCG lying in the middle of the ST segment of the 3D-VCG signal; and
the QRS vector is the vector of the 3D-VCG of maximum magnitude in the terminal portion of the QRS complex of the 3D-VCG signal.

9. The cardiac monitoring system of claim 8 wherein the threshold angle is in the range [130°, 170°] inclusive.

10. The cardiac monitoring system of claim 1 wherein the threshold angle is in the range [130°, 170°] inclusive.

11. The cardiac monitoring system of claim 1 wherein the terminal portion of the QRS complex of the 3D-VCG signal is the last one-third of the QRS complex of the 3D-VCG signal.

12. A non-transitory storage medium storing instructions readable and executable by an electronic data processing device to perform an electrocardiographic (ECG) monitoring method operating on ECG traces acquired from a subject using a plurality of ECG leads, the ECG monitoring method comprising:
determining whether the subject has acute myocardial infarction (AMI) by determining whether:

(i) the ECG traces satisfy an ST Elevation Myocardial Infarction (STEMI) criterion and
(ii) the ECG traces also indicate the subject has a confounding cardiac condition and
(iii) a vector angle difference between an ST vector in the ST segment and a terminal QRS vector of maximum magnitude in a terminal portion of the QRS complex is less than a threshold angle wherein the ST vector and the terminal QRS vector reside in a three-dimensional space defined by an orthogonal set of basis vectors generated from the ECG traces acquired from the subject and wherein the threshold angle is in the range [130°, 170°] inclusive; and
outputting a human-perceptible AMI alarm in response to determining the subject has AMI.

13. The non-transitory storage medium of claim 12 wherein the confounding cardiac condition includes both left bundle branch block (LBBB) and left ventricular hypertrophy (LVH).

14. The non-transitory storage medium of claim 12 wherein the confounding cardiac condition includes Interventricular Conduction Delay (IVCD) indicated by the QRS complex having a duration longer than a threshold duration wherein the threshold duration is at least 100 milliseconds.

15. The non-transitory storage medium of claim 12 wherein condition (iii) is:
(iii) a three-dimensional vector cardiograph (3D-VCG) signal generated from the ECG traces acquired from the subject includes an ST vector in the ST segment of the 3D-VCG signal and a terminal QRS vector of maximum magnitude in a terminal portion of the QRS complex of the 3D-VCG signal for which the angle between the ST vector and the terminal QRS vector is less than a threshold angle.

16. The non-transitory storage medium of claim 15 wherein the 3D-VCG signal is a vector sum of ECG lead vectors in a three-dimensional space.

17. The non-transitory storage medium of claim 12 wherein the ECG monitoring method further comprises:
defining the three-dimensional space in which the ST vector and the terminal QRS vector reside by performing principal component analysis (PCA) to calculate eigenvalues and eigenvectors from the ECG traces acquired from the subject, wherein the orthogonal set of basis vectors comprise the first three eigenvectors generated by the PCA.

18. A method for determining acute myocardial infarction (AMI) comprising:
obtaining ECG traces from a subject;
identifying a deviation of an ST portion of the ECG traces;
converting the ECG traces into a three-dimensional vector cardiogram (3D-VCG) signal having a QRS vector and an ST vector;
calculating a vector angle between the QRS vector and the ST vector; and
classifying the subject as AMI if both (1)the deviation of the ST portion of the ECG traces is greater than a STEMI criteria ST elevation and (2)the calculated vector angle is less than a threshold angle.

19. The method of claim 18 wherein the ST vector corresponds to a middle segment of a single ST portion of the 3D-VCG.

20. The method of claim 18 wherein the QRS vector corresponds to a terminal part of the QRS portion of the 3D-VCG.

21. The method of claim 20 wherein the QRS vector corresponds to the vector of maximum voltage magnitude in the terminal part of the QRS portion of the 3D-VGC.

22. The method of claim 18 wherein the classification step classifies the subject as AMI if the calculated vector angle is less than 150 degrees, and if otherwise, classifies the subject as non-AMI.

23. The method of claim 18 wherein the STEMI criteria ST Elevation is in a range of 0.15 mV to 0.2 mV.

* * * * *